US010709576B2

(12) United States Patent
Shimko et al.

(10) Patent No.: US 10,709,576 B2
(45) Date of Patent: Jul. 14, 2020

(54) BONE MATERIAL DISPENSING APPARATUS AND METHODS

(71) Applicant: Warsaw Orthopedic, Inc., Warsaw, IN (US)

(72) Inventors: Daniel A. Shimko, Germantown, TN (US); Jared J. Diegmueller, Memphis, TN (US); Jonathan M. Dewey, Memphis, TN (US); Kerem N. Kalpakci, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 412 days.

(21) Appl. No.: 15/581,817

(22) Filed: Apr. 28, 2017

(65) Prior Publication Data
US 2018/0311049 A1    Nov. 1, 2018

(51) Int. Cl.
*A61F 2/46* (2006.01)
*A61B 17/88* (2006.01)
*A61B 50/33* (2016.01)
*A61B 17/00* (2006.01)
*A61B 50/30* (2016.01)
*A61B 90/00* (2016.01)

(52) U.S. Cl.
CPC ........ *A61F 2/4601* (2013.01); *A61B 17/8833* (2013.01); *A61B 17/8863* (2013.01); *A61B 50/33* (2016.02); *A61F 2/4644* (2013.01); *A61B 2017/00871* (2013.01); *A61B 2017/8838* (2013.01); *A61B 2050/314* (2016.02); *A61B 2090/0817* (2016.02)

(58) Field of Classification Search
CPC ............ A61B 17/8805; A61B 17/8833; A61B 2017/8838; A61F 2/4601; A61F 2002/4602
USPC ............................... 606/92–94; 222/572–574
See application file for complete search history.

(56) References Cited

U.S. PATENT DOCUMENTS

| 3,255,570 | A | | 6/1966 | Weimer | |
|---|---|---|---|---|---|
| 5,433,256 | A | | 7/1995 | Vasers | |
| 5,588,745 | A | * | 12/1996 | Tanaka | A61B 17/8833 206/222 |
| 6,196,426 | B1 | | 3/2001 | White | |

(Continued)

FOREIGN PATENT DOCUMENTS

| CN | 204779918 U | 11/2015 | |
|---|---|---|---|
| WO | WO-2015132034 A1 * | 9/2015 | ......... A61B 17/8816 |

(Continued)

OTHER PUBLICATIONS

European Search Report for EP 18162779.5 date of completion is Sep. 17, 2018 (10 pages).

*Primary Examiner* — Matthew J Lawson
(74) *Attorney, Agent, or Firm* — Sorell, Lenna & Schmidt, LLP; William D. Schmidt, Esq.

(57) ABSTRACT

A bone material dispensing apparatus for preparing, mixing, and dispensing bone material into a foldable container is provided. In some embodiments, the dispensing apparatus comprises a tray and a foldable container. The tray includes a mixing surface, a dispensing surface and a means to measure the amount of material to be dispensed. A kit including a tray, a foldable container, and a spatula are also provided. A method of using the dispensing apparatus to deliver the bone material to a bone defect is also provided.

13 Claims, 14 Drawing Sheets

(56) References Cited

U.S. PATENT DOCUMENTS

| | | |
|---|---|---|
| 6,364,519 B1 | 4/2002 | Hughes et al. |
| 6,582,438 B2 | 6/2003 | DeMayo |
| 8,685,031 B2 | 4/2014 | Kleiner et al. |
| 8,795,365 B2 | 8/2014 | Arcenio et al. |
| 8,900,620 B2 | 12/2014 | Fulmer et al. |
| 9,033,994 B2 | 5/2015 | Fingerhut |
| 9,101,475 B2 | 8/2015 | Wei et al. |
| 9,101,606 B2 | 8/2015 | Drapeau et al. |
| 9,220,598 B2 | 12/2015 | Betz et al. |
| 9,333,082 B2 | 5/2016 | Wei et al. |
| 9,394,152 B2 | 7/2016 | Connellan et al. |
| 9,492,278 B2 | 11/2016 | Wei et al. |
| 2002/0112981 A1 | 8/2002 | Cooper et al. |
| 2005/0155901 A1 | 7/2005 | Krueger et al. |
| 2010/0179507 A1* | 7/2010 | Hess ................. A61B 17/8833 604/500 |
| 2011/0015640 A1 | 1/2011 | Hess et al. |
| 2011/0054408 A1 | 3/2011 | Wei et al. |
| 2011/0060227 A1* | 3/2011 | Saadat ................. A61B 1/0008 600/476 |
| 2012/0065613 A1 | 3/2012 | Pepper et al. |
| 2014/0263389 A1 | 9/2014 | Perozek et al. |
| 2016/0038207 A1 | 2/2016 | Wei et al. |
| 2016/0250038 A1 | 9/2016 | Wei et al. |
| 2018/0250145 A1* | 9/2018 | Stevenson ............. A61F 2/4644 |

FOREIGN PATENT DOCUMENTS

| | | | |
|---|---|---|---|
| WO | WO2015132034 A1 | 9/2015 | |
| WO | WO-2019040851 A1 * | 2/2019 | ......... A61B 17/3472 |

\* cited by examiner

BONE MATERIAL DISPENSING APPARATUS AND METHODS

BACKGROUND

Mammalian bone tissue contains one or more proteinaceous materials, presumably active during growth and natural bone healing that can induce a developmental cascade of cellular events resulting in bone formation. Various developmental factors are present in bone. These include bone morphogenetic proteins (BMPs), bone inductive proteins, bone growth factors, osteogenic proteins, or osteoinductive proteins. While these proteins have different effects and functions, these proteins will be referred to collectively herein as osteoinductive factors.

These osteoinductive factors are present within the compound structure of cortical bone and are present at very low concentrations, for example, 0.003% by weight. Osteoinductive factors direct the differentiation of pluripotent mesenchymal cells into osteoprogenitor cells that form osteoblasts. Proper demineralization of cortical bone exposes these osteoinductive factors in bone rendering it osteoinductive.

The rapid and effective repair of bone defects caused by injury, disease, wounds, or surgery has long been a goal of orthopedic surgery. Toward this end, a number of materials have been used or proposed for use in the repair of bone defects. The biological, physical, and mechanical properties of the materials are among the major factors influencing their suitability and performance in various orthopedic applications.

Autologous cancellous bone (ACB) has long been considered the gold standard for bone grafts. ACB includes osteogenic cells, which have the potential to assist in bone healing, is nonimmunogenic, and has structural and functional characteristics that are appropriate for a healthy recipient. Some people do not have adequate amounts of ACB for harvesting. These people include, for example, older people and people who have had previous surgeries. A majority of people, however, do have adequate amounts of ACB for harvesting. There may nevertheless be reluctance to harvest ACB because of pain at the harvest site and potential donor site morbidity.

Conventionally, bone tissue regeneration is achieved by filling a bone defect with a bone material, for example, a bone graft. Over time, the bone graft is incorporated by the host and new bone remodels the bone graft. Bone material can include bone from the patient's own body or artificial, synthetic, or natural substitute bone material.

Demineralized bone matrix (DBM) is bone material commonly used in orthopedic procedures to substitute for, or extend the volume of, an autograft or allograft bone. Demineralized bone matrix is typically derived from cadavers. The bone is removed aseptically and/or treated to kill any infectious agents. The bone is then particulated by milling or grinding and then the mineral components are extracted, for example, by soaking the bone in an acidic solution.

To deliver the bone material to the bone defect, often times the bone material is mixed with liquid or a therapeutic agent, powder, fiber or granular material. Mixing devices that are currently available are cumbersome to use and do not allow uniform and easy mixing of material. Further, transfer of bone material to the delivery device is often done by crude packing of the bone delivery device and there is unwanted spillage of bone material out of the device, which may increase the risk of contamination of the bone material. Currently available delivery devices often lack precision in measuring the bone material for delivery to the target bone defect.

It would therefore be desirable to provide a bone material dispensing apparatus that allows easy and precise measuring and mixing of bone material. Further, a bone material dispensing apparatus that allows easier loading of the delivery device, which reduces the risk of contamination and spillage of bone material from the delivery device would also be desirable.

SUMMARY

In some embodiments, there is a bone material dispensing apparatus that allows easy precision measuring and mixing of bone material. The bone material dispensing apparatus allows easier loading of the delivery device, which reduces the risk of contamination and spillage of bone material. In some embodiments, the bone material dispensing apparatus allows uniform mixing and measuring of the bone material, reducing clogging and friction resistance in the bone material dispensing apparatus.

In some embodiments, there is a bone material dispensing apparatus, comprising: a tray having a proximal end, a distal end, and a bone material dispensing surface disposed between the proximal end and the distal end of the tray; a foldable container configured to removably engage the proximal end of the tray, the foldable container being movable in a folded configuration and an unfolded configuration about a fold line in the foldable container, the foldable container having an upper compartment and a lower compartment, the lower compartment of the foldable container configured to receive a bone material from the dispensing surface of the tray when the foldable container removably engages the proximal end of the tray in the unfolded configuration and when the foldable container is in the folded configuration, the upper compartment is configured to enclose the bone material in the lower compartment.

In some embodiments, there is a kit for dispensing bone material, the kit comprising: a tray having a proximal end, a distal end, and a bone material dispensing surface disposed between the proximal end and the distal end of the tray, the dispensing surface comprising a plurality of ridges extending from the distal end of the tray to a region adjacent to the proximal end of the tray, each of the plurality of ridges having a side wall and each of the plurality of ridges spaced a distance apart from each other such that a measured amount of a bone material can be placed between each side wall of at least two of the plurality of ridges for measured dispensing of the bone material; a foldable container configured to removably engage the proximal end of the tray, the foldable container being movable in a folded configuration and an unfolded configuration about a fold line in the foldable container, the foldable container having an upper compartment and a lower compartment, the lower compartment of the foldable container configured to receive bone material from the dispensing surface of the tray when the foldable container removably engages the proximal end of the tray in the unfolded configuration and when the foldable container is in the folded configuration, the upper compartment is configured to enclose the bone material in the lower compartment, wherein the proximal end of the tray comprises a first channel and a second channel configured to hold the upper compartment and the lower compartment of the foldable container, the first channel of the proximal end of the tray dimensioned to correspond to the upper compartment of the foldable container and the second channel of the proximal end of the tray dimensioned to correspond to the lower compartment of the foldable container such that at least in the unfolded configuration, the foldable container is held by the tray; and a spatula configured to dispense bone material from the dispensing surface into the foldable container.

In some embodiments, there is a method of filling bone material into a foldable container, the method comprising: placing a bone material in or on a dispensing surface of a tray, the tray having a proximal end, a distal end, and the dispensing surface disposed between the proximal end and the distal end of the tray; transferring the bone material from the dispensing surface of the tray to fill a foldable container with the bone material, the foldable container configured to removably engage the proximal end of the tray, the foldable container being movable in a folded configuration and an unfolded configuration about a fold line in the foldable container, the foldable container having an upper compartment and a lower compartment, the lower compartment of the foldable container configured to receive the bone material from the dispensing surface of the tray when the foldable container removably engages the proximal end of the tray in the unfolded configuration; and folding the upper compartment on the lower compartment of the foldable container to enclose the bone material in the foldable container when the foldable container is in the folded configuration thereby filling the foldable container with bone material.

While multiple embodiments are disclosed, still other embodiments of the present disclosure will become apparent to those skilled in the art from the following detailed description. As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent with regard to the following description, appended claims and accompanying figures where:

Figure 1:
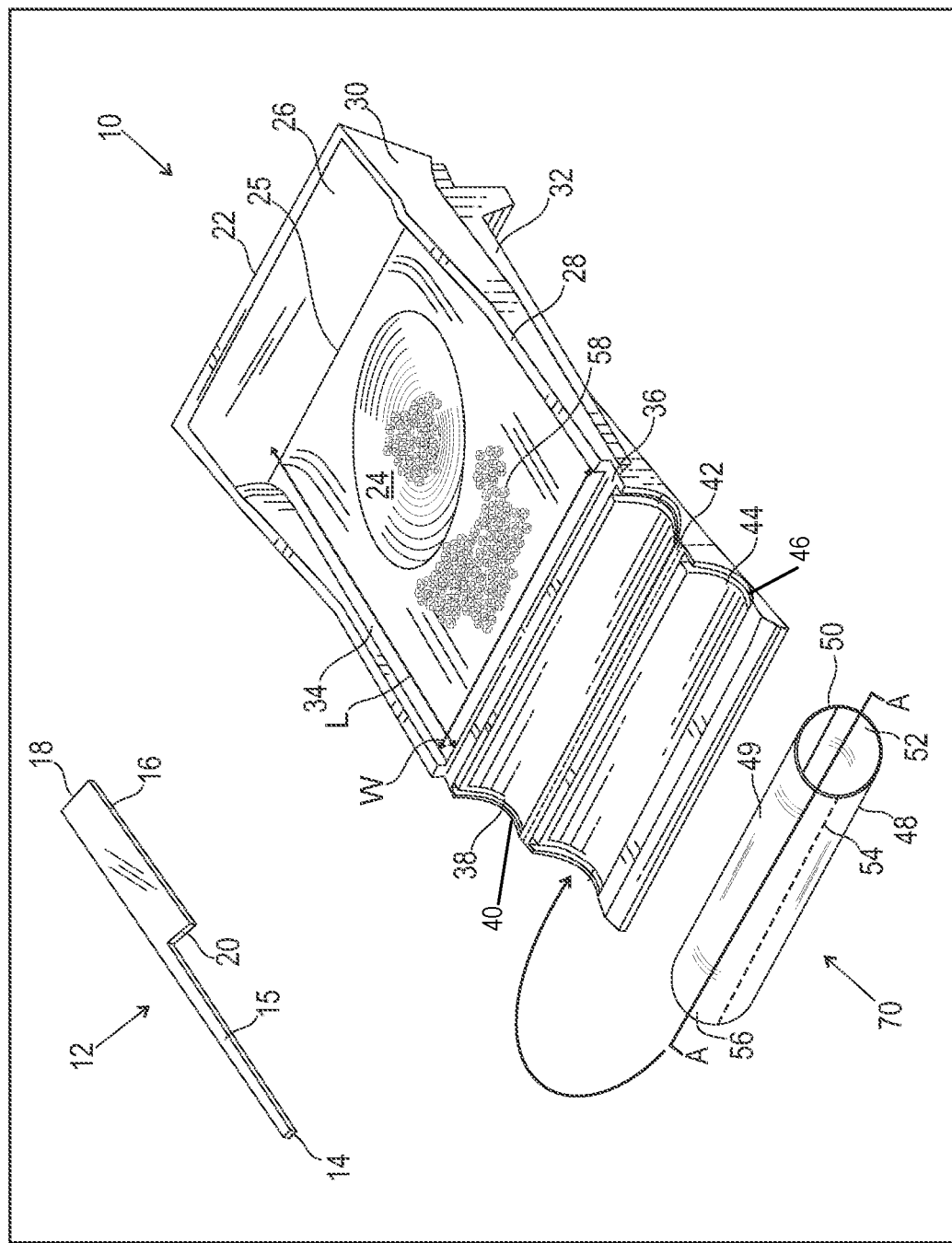
FIG. 1 depicts a perspective view of a bone material dispensing apparatus according to an aspect of the present application, where the foldable container is in a folded configuration and the tray contains some bone material.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

It is noted that, as used in this specification and the appended claims, the singular forms "a," "an," and "the," include plural referents unless expressly and unequivocally limited to one referent. For example, reference to "a container" includes one, two, three or more containers.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "xenograft" refers to tissue or organs from an individual of one species transplanted into or grafted onto an organism of another species, genus, or family.

The term "mammal" refers to organisms from the taxonomy class "mammalian," including, but not limited to, humans; other primates, such as chimpanzees, apes, orangutans and monkeys; rats, mice, cats, dogs, cows, horses, etc.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "bone material" includes natural and/or inorganic material such as, for example, inorganic ceramic and/or bone substitute material. The bone material can also include natural bone material such as, for example, bone which is cortical, cancellous or cortico-cancellous of autogenous, allogenic, xenogenic, or transgenic origin. In some embodiments, bone material can include demineralized bone material such as, for example, substantially demineralized bone material, partially demineralized bone material, or fully demineralized bone material.

"Demineralized" as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the application. In some embodiments, demineralized bone has less than 95% of its original mineral content.

In some embodiments, demineralized bone has less than 95% of its original mineral content. In some embodiments, demineralized bone has less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "demineralized" is intended to encompass such expressions as "substantially demineralized," "superficially demineralized," "partially demineralized," "surface demineralized," and "fully demineralized."

"Partially demineralized" is intended to encompass "surface demineralized." "Partially demineralized bone" is intended to refer to preparations with greater than 5% calcium by weight but containing less than 100% of the original starting amount of calcium. In some embodiments, partially demineralized comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

"Superficially demineralized" as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

"Demineralized bone matrix" as used herein, refers to any material generated by removing mineral material from bone tissue. In preferred embodiments, the DBM compositions as used herein include preparations containing less than 5% calcium and preferably less than 1% calcium by weight.

"Biocompatible" as used herein, refers to materials that, upon administration in vivo, do not induce undesirable long-term effects.

"Osteoconductive" as used herein, refers to the ability of a non-osteoinductive substance to serve as a suitable template or substance along which bone may grow.

"Osteogenic", as used herein, refers to the ability of an agent, material, or implant to enhance or accelerate the growth of new bone tissue by one or more mechanisms such as osteogenesis, osteoconduction, and/or osteoinduction.

"Osteoinductive" as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

The terms "upper", "lower", "top", "bottom", "side", "proximal", "distal" and so forth have been used herein merely for convenience to describe the present invention and its parts as oriented in the drawings. It is to be understood, however, that these terms are in no way limiting to the disclosure since the delivery systems described herein may obviously be disposed in different orientations when in use.

The term "removably engage" includes engagement of two or more components that can be used or combined into one element via the engagement of the two or more elements with a connecting means, a locking means, or by placing the elements tightly together. The two or more elements may be positioned adjacent to each other and each include a contacting surface. For example, a foldable container may be placed adjacent to the proximal end of the tray such that the foldable container removably engages the tray. In some embodiments, the foldable container may snap fit into the proximal end of the tray such that the foldable container removably engages the tray.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention is an approximation, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the disclosure, examples of which are illustrated in the accompanying figures. While the disclosure will be described in conjunction with the illustrated embodiments, it will be understood that they are not intended to limit the disclosure to those embodiments. On the contrary, the disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

Bone Material

In some embodiments, there is a bone material dispensing apparatus that allows easy precision measuring and mixing of bone material. The bone material dispensing apparatus allows easier loading of the delivery device, which reduces the risk of contamination and spillage of bone material. In some embodiments, the bone material dispensing apparatus allows uniform mixing and measuring of the bone material, reducing clogging and friction resistance in the bone material dispensing apparatus. The bone material can be in granular, paste, putty or powder forms.

In some embodiments, the bone material can be demineralized bone material. The demineralized bone material can comprise demineralized bone, powder, chips, granules, shards, fibers or other shapes having irregular or random geometries. These can include, for example, substantially demineralized, partially demineralized, or fully demineralized cortical and cancellous bone. These also include surface demineralization, where the surface of the bone construct is substantially demineralized, partially demineralized, or fully demineralized, yet the body of the bone construct is fully mineralized. The configuration of the bone material can be obtained by milling, shaving, cutting or machining whole bone as described in, for example, U.S. Pat. No. 5,899,939. The entire disclosure is herein incorporated by reference into the present disclosure.

In some embodiments, the bone material can comprise elongated demineralized bone fibers having an average length to average thickness ratio or aspect ratio of the fibers from about 50:1 to about 1000:1. In overall appearance the elongated demineralized bone fibers can be round, spherical, granular, elongated, powders, chips, fibers, cylinders, threads, narrow strips, thin sheets, or a combination thereof. In some embodiments, the bone material comprises elongated demineralized bone fibers and chips. In some embodiments, the bone material comprises fully demineralized fibers and surface demineralized chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the bone material comprises demineralized bone matrix fibers and demineralized bone matrix chips in a 30:60 ratio. In some embodiments, the bone material comprises demineralized bone matrix fibers and demineralized bone matrix chips in a ratio of 25:75 to about 75:25 fibers to chips.

In some embodiments, the bone material can be an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the bone material can comprise mineral particles, which comprise tricalcium phosphate and hydroxyapatite in a ratio of about 80:20 to about 90:10. In some embodiments, the mineral particles can comprise tricalcium phosphate and hydroxyapatite in a ratio of about 70:30 to about 95:5. In some embodiments, the mineral particles can comprise tricalcium phosphate and hydroxyapatite in a ratio of about 85:15.

In some embodiments, the bone material may be seeded with harvested bone cells and/or bone tissue, such as for example, cortical bone, autogenous bone, allogenic bones and/or xenogeneic bone while it is mixed.

In some embodiments, the bone material may be mixed with one or more therapeutic agents, for example, an anti-inflammatory agent, an analgesic agent, an osteoinductive growth factor, an antimicrobial agent or a combination thereof. Osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof. Recombinant BMP-2 can be used at a concentration of about 0.4 mg/mL to about 10.0 mg/mL, preferably about 1.5 mg/mL.

The bone material may include or be mixed with one or more members from the TGF-β superfamily. For example, the matrix may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The bone material may include or be mixed with a therapeutic agent including, but not limited to, IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. The bone material may include or be mixed with therapeutic agents including excitatory amino acids such as glutamate and aspartate, antagonists or inhibitors of glutamate binding to NMDA receptors, AMPA receptors, and/or kainate receptors. The bone material may include or be mixed with therapeutic agents to reduce inflammation including but not limited to interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), or aurin-tricarboxylic acid (which inhibits TNF-α).

The bone material may include or be mixed with a therapeutic agent including, but not limited to, an analgesic agent. Examples of analgesic agents include, but are not limited to, acetaminophen, tramadol, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, meperidine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The bone material may include or be mixed with a therapeutic agent including, but not limited to, an anti-inflammatory agent. An example of an anti-inflammatory agent includes, but is not limited to, clonidine, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof.

Anti-inflammatory agents also include steroids, such as for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The bone material may include or be mixed with a therapeutic agent including, but not limited to, a statin. Examples of a useful statin include, but are not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In some embodiments, the bone material can include an antimicrobial agent. In some embodiments, the antimicrobial agent can include one or more of triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, or combinations thereof.

Examples of antimicrobial agents include, by way of illustration and not limited to, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz, sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

The antimicrobial agent in the bone material can be an antiviral agent that can be mixed with the bone material. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Dispensing Apparatus

In some embodiments, there is a bone material dispensing apparatus, comprising: a tray having a proximal end, a distal end, and a bone material dispensing surface disposed between the proximal end and the distal end of the tray; a foldable container configured to removably engage the proximal end of the tray, the foldable container being movable in a folded configuration and an unfolded configuration about a fold line in the foldable container, the foldable container having an upper compartment and a lower compartment, the lower compartment of the foldable container configured to receive a bone material from the dispensing surface of the tray when the foldable container removably engages the proximal end of the tray in the unfolded configuration and when the foldable container is in the folded configuration, the upper compartment is configured to enclose the bone material in the lower compartment. In some embodiments, the upper compartment and the lower compartment can be configured to engage the tray at the same time and receive bone material simultaneously. In some embodiments, the upper compartment and the lower compartment can engage the tray at the same time.

Referring to FIG. 1, it illustrates a bone material dispensing apparatus 10 of the present application. The bone material dispensing apparatus 10 comprises a tray 22 configured to receive a foldable container 70. The tray 22 comprises a proximal end 36, a distal end 25 bordered by a back wall 26, a side edge 28 bordered by a side wall 30, and a bottom exterior surface 32. The tray 22 comprises a mixing surface 24 disposed between the proximal end 36 and the distal end 25 to mix the bone material and other components together (e.g., therapeutic agent, diluent, blood, cells, etc.). The mixing surface 24 can have a bowl configuration to allow mixing solids and liquid components of the bone material. Adjacent to the proximal end 36 of the tray 22 is a dispensing surface 34 to dispense the bone material into an upper compartment 49 and/or a lower compartment 48 of the foldable container 70. The dispensing surface 34 has a length L and a width W, which allows a measured amount of bone material to be dispensed. In the embodiment shown, the bone material is shown as granules 58. However, it will be understood by those of ordinary skill in the art that the bone material can be in other forms (e.g., a powder, paste, putty, liquid, gel, etc.). In some embodiments, the proximal end 36 of the tray 22 comprises first channel 38 and second channel 44. The first channel 38 of the proximal end 36 of the tray 22 is dimensioned to correspond to the upper compartment 49 of the foldable container 70 and the second channel 44 of the proximal end 36 of the tray 22 is dimensioned to correspond to the lower compartment 48 of the foldable container 70 such that at least in the unfolded configuration (shown in FIG. 2) the foldable container 70 is held by the tray 22.

The first channel 38 and the upper compartment 49 could share a similar geometry such that the upper compartment 49 fits securely inside the first channel 38 during the filling of the bone materials. The second channel 44 and the lower compartment 48 could share similar geometry to fit securely inside the second channel 44 during the filling of the bone materials. The first channel 38 and the second channel 44 can have different geometry than the upper compartment 49 and the lower compartment 48, but still be shaped to provide a sufficient constrain to the foldable container 70 during the filling of bone materials.

The first channel 38 comprises a proximal end 40. The second channel 44 comprises a distal end 46. The first channel 38 and the second channel 44 have an elongated configuration to correspond to the tubular configuration of the foldable container 70 having longitudinal axis A. A ridge 42 of the tray 22 separates the first channel 38 and the second channel 44. In use, the user can slide the upper compartment 49 of the foldable container 70 into the first channel 38 at the proximal end 40 of the first channel 38 and the lower compartment 48 of the foldable container 70 can slide into the second channel 44 and contact the distal end 46 of the second channel 44 so that the tray 22 holds the foldable container 70 and allows filling of the foldable container 70 with bone material when it is in an unfolded configuration.

The ridge 42 of the tray 22 is dimensioned to align with a fold line 54 of the foldable container 70. Distal end 52 of the foldable container 70 can engage with the distal end 46 of the second channel 44 and proximal end 56 of the foldable container 70 can engage with the proximal end 40 of the first channel 38 when the foldable container 70 is in an unfolded or open configuration. Shown in FIG. 1, the foldable container 70 is in a folded or closed configuration and upper compartment 49 of the foldable container 70 contacts the lower compartment 48 of the foldable container 70 where an openable seam 50 extends along longitudinal axis A. In some embodiments, the ridge 42 is separable such that the first channel 38 and the second channel 44 can detach from each other, leaving only one channel engaging the tray 22. In some embodiments, the proximal end and the distal end of the first channel and the second channel may have additional constraining mechanisms such as an additional wall or bar to constrain the foldable container 70 during loading of the material.

To mix components and/or dispense the bone material, bone material dispensing apparatus 10, in some embodiments, comprises a spatula 12. The spatula 12 comprises a body 15 comprising a distal end 14 and a blade portion 20 comprising a blade edge 16. In some embodiments, the blade or blade edge 16 has a plurality of projections spaced a distance apart from each other, each projection configured to engage a plurality of ridges of the tray 22, as described herein. The spatula 12 further comprises a tip portion 18 to aid in dispensing the bone material into the foldable container 70 by contact with the bone material, the mixing surface 24 and the dispensing surface 34.

Figure 2:
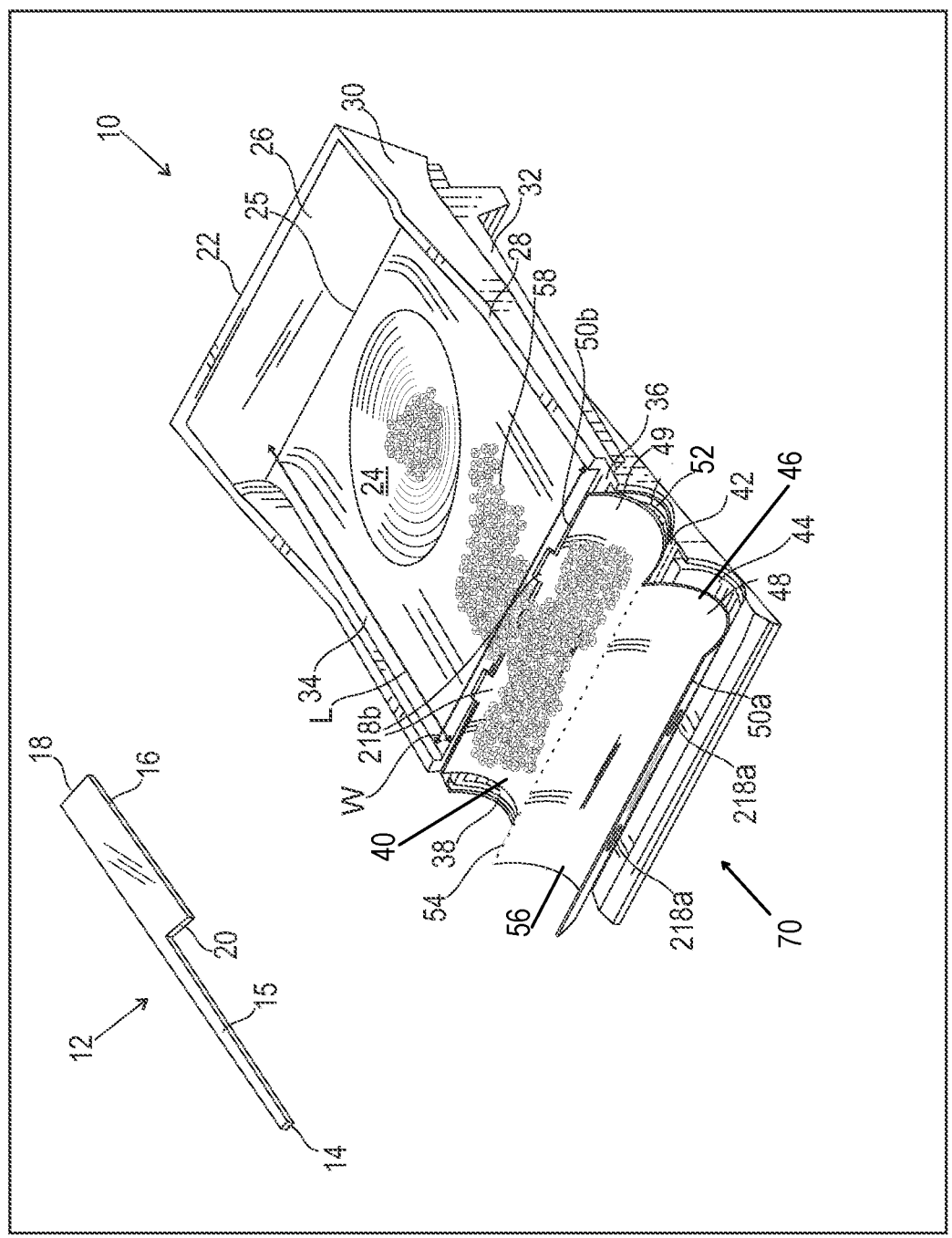
FIG. 2 depicts a perspective view of a bone material dispensing apparatus of FIG. 1 where the foldable container is in an unfolded configuration and the foldable container is loaded with some bone material.

Referring to FIG. 2, it illustrates a bone material dispensing apparatus 10 of the present application. The bone material dispensing apparatus 10 comprises a tray 22 that has the foldable container 70 shown in an unfolded configuration. The tray 22 comprises a proximal end 36, a distal end 25 bordered by a back wall 26, a side edge 28 bordered by a side wall 30, and a bottom exterior surface 32. The tray 22 comprises a mixing surface 24 disposed between the proximal end 36 and distal end 25 to mix the bone material and other components together. Adjacent to the proximal end 36 of the tray 22 is a dispensing surface 34 to dispense the bone material shown as granules 58 into the upper compartment 49 and/or lower compartment 48 of the foldable container 70. The dispensing surface 34 has a length L and a width W, which allows a measured amount of bone material to be dispensed. In the embodiment shown, the granules 58 are disposed into the upper compartment 49 of the foldable container 70 to partially fill the foldable container 70. The first channel 38 of the proximal end 36 of the tray 22 holds the upper compartment 49 of the foldable container and the second channel 44 of the proximal end 36 of the tray 22 holds the lower compartment 48 of the foldable container 70 in the unfolded configuration.

The first channel 38 comprises a proximal end 40. The second channel 44 comprises a distal end 46. A ridge 42 of the tray 22 separates the first channel 38 and the second channel 44. In use, the user can slide the upper compartment 49 of the foldable container 70 into the first channel 38 of the proximal end 36 of the tray 22 and the lower compartment 48 of the foldable container 70 can slide into the second channel 44 of the proximal end 36 of the tray so that the tray 22 holds the foldable container 70 and allows filling of the foldable container 70 with bone material 58 when it is in an unfolded configuration. The ridge 42 of the tray 22 is dimensioned to align with fold line 54 of the foldable container 70. Distal end 52 of the foldable container 70 is engaged with the first channel 38 and proximal end 56 of the foldable container 70 is engage with the second channel 44 when the foldable container 70 is in an unfolded configuration. In some embodiments, the channels of the tray may be configured to the shape of the foldable container so as to allow ease of insertion of the foldable container in the channels and allow stability of the device.

The foldable container 70, in the embodiment shown, comprises two edges, a first edge 50a and a second edge 50b. The first edge 50a is on the lower compartment 48 and the second edge 50b is on the upper compartment 49 of the foldable container 70. Each edge has a locking mechanism to lock the upper compartment 49 and lower compartment 48 together. The locking mechanism includes slots 218a, which are adjacent first edge 50a and are spaced apart and correspond to tabs 218b, which are also spaced apart and adjacent second edge 50b. To lock the foldable container 70, first edge 50a and second edge 50b are brought together causing the foldable container 70 to fold via fold line 54, and tabs 218b project outwardly from the exterior to engage and lock into slots 218a to lock the foldable container 70 in a folded configuration. In some embodiments, the locking mechanism can be alternating tabs and slots to allow locking and can include friction fitting or snap fittings. It will be understood that the locking mechanism is an optional feature.

In some embodiments, the foldable container 70 can be made of a memory shape polymer and/or alloy to allow the foldable container 70 to move from an unfolded configuration to a folded configuration without the need for a locking mechanism. In some embodiments, a memory shape material may be used in the tray and/or foldable container 70, such as a memory shape polymer or alloys. Memory shape polymers include, but are not limited to polyethers, polyacrylates, polyamides, polysiloxanes, polyurethanes, polyethers amides, polyurethane/ureas, polyether esters, polynorborene, cross-linked polymers such as cross-linked polyethylene and cross-linked poly(cyclooctene), inorganic-organic hybrid polymers, and copolymers such as urethane/butadiene copolymers, styrene-butadiene copolymers. Memory shape alloys include, but are not limited to TiNi, CuZnAl, and FeNiAl alloys. In some embodiments, the foldable container 70 and/or tray can be fabricated by injection molding of plastic materials comprising rigid, surgical grade plastic and/or metal materials.

To mix components and/or dispense the bone material, the bone material dispensing apparatus 10, in some embodiments, comprises a spatula 12. The spatula 12 comprises a body 15 comprising a distal end 14 and a blade portion 20 comprising a blade edge 16. The spatula 12 further comprises a tip portion 18 to aid in dispensing the bone material into the foldable container 70 by contact with the bone material, the mixing surface 24 and the dispensing surface 34 of tray 22.

Figure 3:
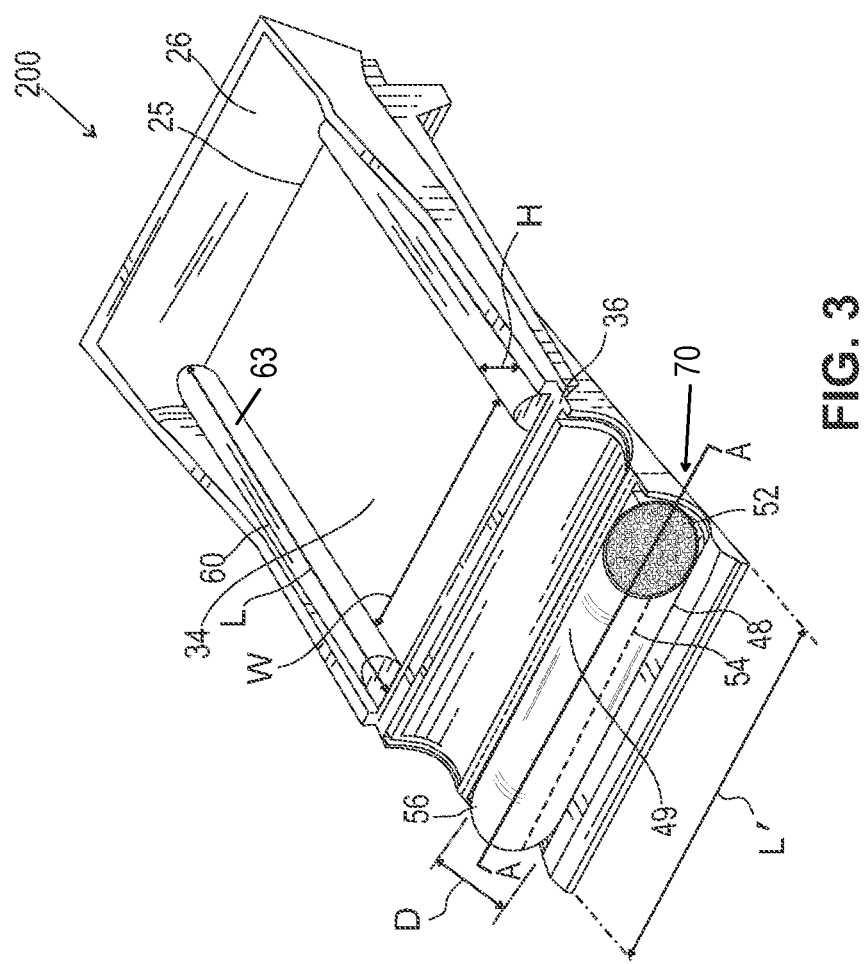
FIG. 3 depicts a perspective view of a bone material dispensing apparatus according to another aspect of the present application where the foldable container is in a folded configuration and the foldable container partially encloses bone material.

Referring to FIG. 3, it illustrates another embodiment of a bone material dispensing apparatus of the present application. The bone material dispensing apparatus comprises a tray 200 that has the foldable container 70 shown in a folded configuration. The tray 200 comprises a proximal end 36, a distal end 25 bordered by a back wall 26. The tray 200 comprises a dispensing surface 34, which can have a decline extending from the distal end 25 to the proximal end 36 of the tray 200. This allows easier movement of the bone material from the distal end 25 to the proximal end 36 of the tray 200. In the embodiment shown, the dispensing surface 34 has a plurality of ridges 60 disposed on the dispensing surface 34. Each ridge has a length L and a height H. Each ridge extends longitudinally along its length between the distal end 25 and the proximal end 36 of the tray 200. Each ridge has a side wall 63, which is spaced a distance apart from each other indicated by the W such that a measured amount of bone material can be placed between each side wall for measured dispensing of the bone material into the foldable container 70.

For example, the foldable container 70 has a diameter D and a length L'. In some embodiments, the product of length, width and height equals the product of π, the square of the diameter and the length of the channel divided by 4. In other words, $WDL' = \pi D^2 L'/4$. Knowing this calculation, a measured amount of the bone material can be loaded into the foldable container 70 because the volume of bone material that can fit between each ridge would be a predetermined amount.

In the embodiment shown in FIG. 3, the foldable container 70 is in a folded configuration via fold line 54 that can be, for example, a hinge or other rotatable fitting, that allows the upper compartment 49 and the lower compartment 48 of the foldable container 70 to be folded and partially enclose the bone material. The foldable container 70 has an opening at the distal end 52 and an opening at the proximal end 56. These openings, in some embodiments, can be configured to receive a plunger and the plunger would extend along longitudinal axis A.

Figure 4:
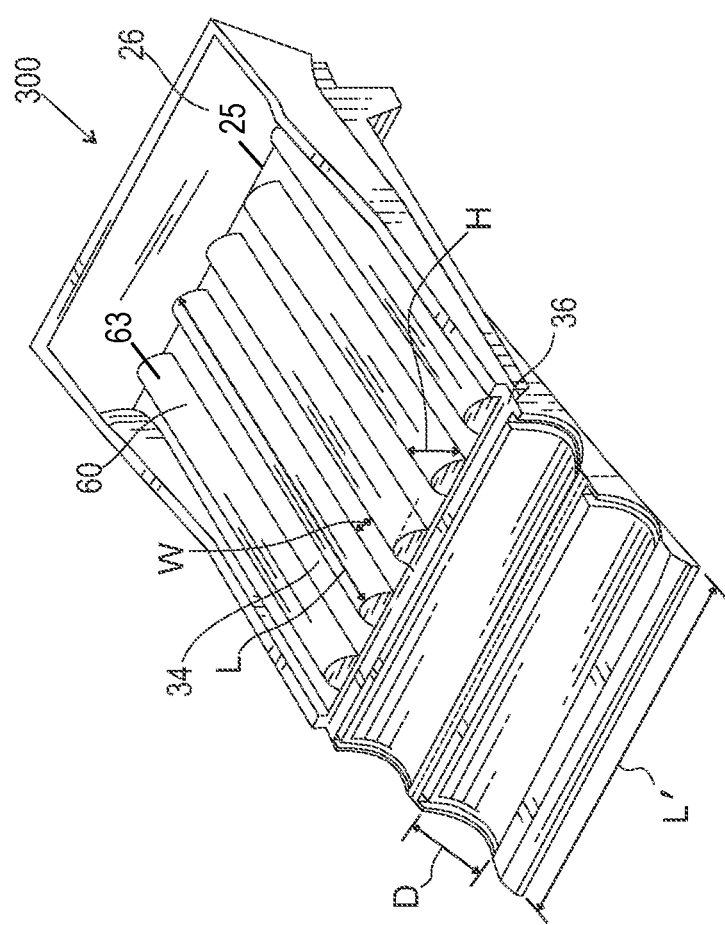
FIG. 4 depicts a perspective view of a bone material dispensing apparatus according to another aspect of the present application where the tray has ridges for measured dispensing of bone material.

Referring to FIG. 4, it illustrates another embodiment of the tray 300 that is configured to receive a foldable container (not shown). The tray 300 comprises a back wall 26 that can have a declining surface extending from the distal end 25 of the tray. The tray comprises a dispensing surface 34, which can also have a declining surface extending from distal end 25 to the proximal end 36 of the tray 300. This declining surface can be from about 2 degrees, 3 degrees, 4 degrees, 5 degrees to about 6 degrees. In the embodiment shown, the dispensing surface 34 has a plurality of ridges 60 disposed on the dispensing surface 34. Each ridge has a length L and a height H. Each ridge extends longitudinally along its length between the distal end 25 to the proximal end 36 of the tray 300. Each ridge has a side wall 63, which is spaced a distance apart from each other indicated by the W such that a measured amount of bone material can be placed between each side wall for measured dispensing of the bone material into the foldable container. There are multiple ridges and multiple widths (W, $W_1$, $W_2$ ... $W_n$). The first channel at the proximal end 36 has a diameter D and a length L'. The product of length, the sum of all widths and heights equal the product of π, the square of the diameter and the length of the channel divided by 4. In other words, $L(W+W_1+W_2 \ldots W_n)H = \pi D^2 L'/4$. Thus, the user can place the bone material between one or more ridges and those ridges will be configured to have a predetermined amount of bone material to be disposed between them. In this way, a measured amount of bone material can be dispensed from the tray 300. In some embodiments, there can be an index marker (not shown) disposed between ridges to provide a visual indicator to a user of the amount of bone material and/or therapeutic agent (e.g., 5 g, 6 g, 7 g, etc.) that can be disposed between the plurality of ridges 60 to be dispensed.

In some embodiments, the foldable container and/or the tray comprise additional measuring structures such as multiple channels and/or ridges to segregate the granules 58 into defined, smaller quantities. These additional measuring structures can further aid in spreading the granules 58 evenly along the axis of the foldable container 70 and prevent packing of the granules 58 too tightly, thus facilitating easier introduction of the granules 58 out of the foldable container 70 and into a device or targeted location.

Figure 5:
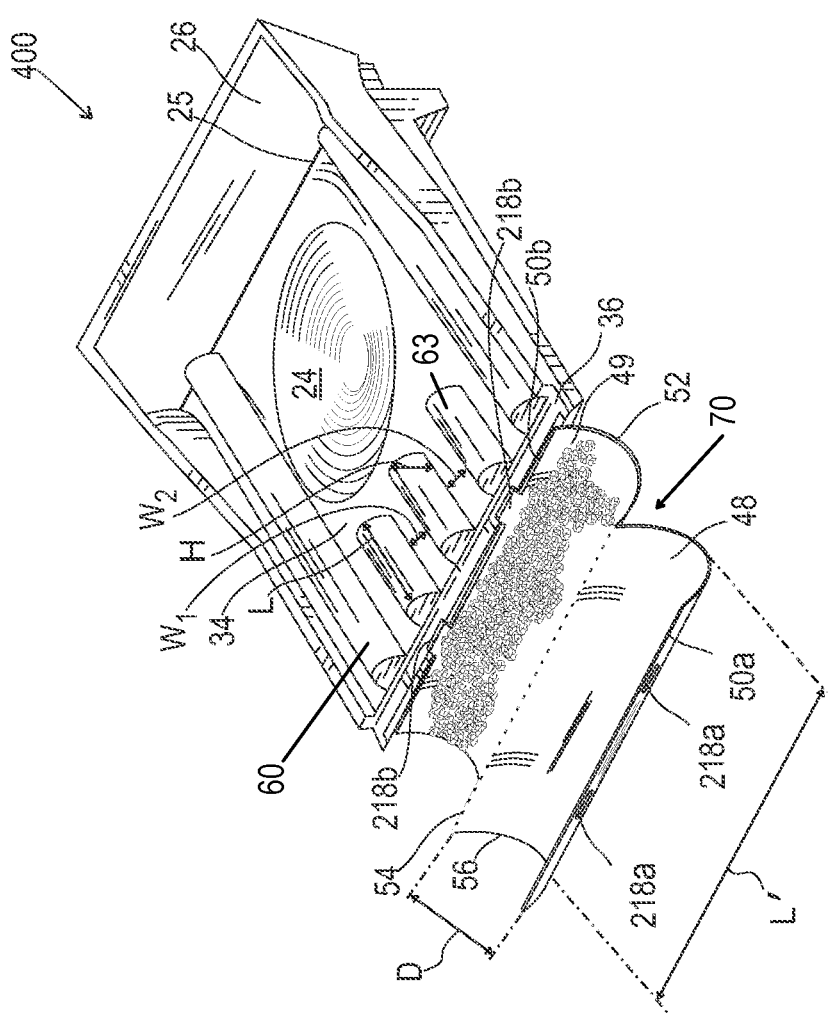
FIG. 5 depicts a perspective view of a bone material dispensing apparatus according to another aspect of the present application where the foldable container is in an unfolded configuration and the foldable container is loaded with some bone material.

Referring to FIG. 5, it illustrates another embodiment of a bone material dispensing apparatus of the present application. The bone material dispensing apparatus comprises a tray 400 that has the foldable container 70 in an unfolded configuration. The tray 400 comprises a proximal end 36, a distal end 25 bordered by a back wall 26. The tray 400 comprises a dispensing surface 34 extending from the distal end 25 to the proximal end 36 of the tray 400 and a mixing surface 24 shown as a bowl configuration to allow mixing of the bone material. In the embodiment shown, the dispensing surface 34 has a plurality of ridges 60 disposed on the dispensing surface 34. Each ridge has a length L and a height H. Each ridge extends longitudinally along its length between the distal end 25 and the proximal end 36 of the tray 400. Each ridge has a side wall 63, which is spaced a distance apart from each other indicated by the $W_1$ or $W_2$, such that a measured amount of bone material can be placed between each side wall for measured dispensing of the bone material into the foldable container 70. In the embodiment shown, there are multiple ridges and multiple widths ($W_1$, $W_2 \ldots W_n$). The foldable container 70 having distal end 52 and proximal end 56 is shown in an unfolded configuration and the foldable container 70 has a diameter D and a length L'. The product of length, the sum of all widths and heights equals the product of π, the square of the diameter and the length of the channel divided by 4. In other words, $L(W_1 + W_2 \ldots W_n)H = \pi D^2 L'/4$. Thus, the user can place the bone material between one or more ridges and those ridges will be configured to have a predetermined amount of bone material to be disposed between them. In this way, a measured amount of bone material can be dispensed from the tray. It will be understood that in some embodiments, the plurality of ridges 60 may have different lengths and widths and appear as different patterns on the dispensing surface 34 of the tray 400.

The foldable container 70, in the embodiment shown, comprises two edges, a first edge 50a and a second edge 50b. The first edge 50a is on the lower compartment 48 and the second edge 50b is on the upper compartment 49 of the foldable container 70. The edges have a locking mechanism to lock the upper compartment 49 and lower compartment 48 together. The locking mechanism includes slots 218a, which are adjacent first edge 50a and are spaced apart and correspond to tabs 218b, which are also spaced apart and adjacent second edge 50b. To lock the foldable container 70, first edge 50a and second edge 50b are brought together causing the foldable container 70 to fold via fold line 54 and tabs 218b project outwardly from the exterior to engage and lock into slots 218a to lock the foldable container 70 in a folded configuration. In some embodiments, there is a locking mechanism such as snap-fit or tab-slot fitting to removable engage the tray 400 and the foldable container 70 such that the tray 400 and the foldable container 70 can be removably attached to the tray 400 and provide stability during the dispensing process. In the embodiment shown in FIG. 5, the foldable container 70 engages the tray 400 by its tabs 218b and there are no channels to hold the tray in the desired position.

Figure 6:
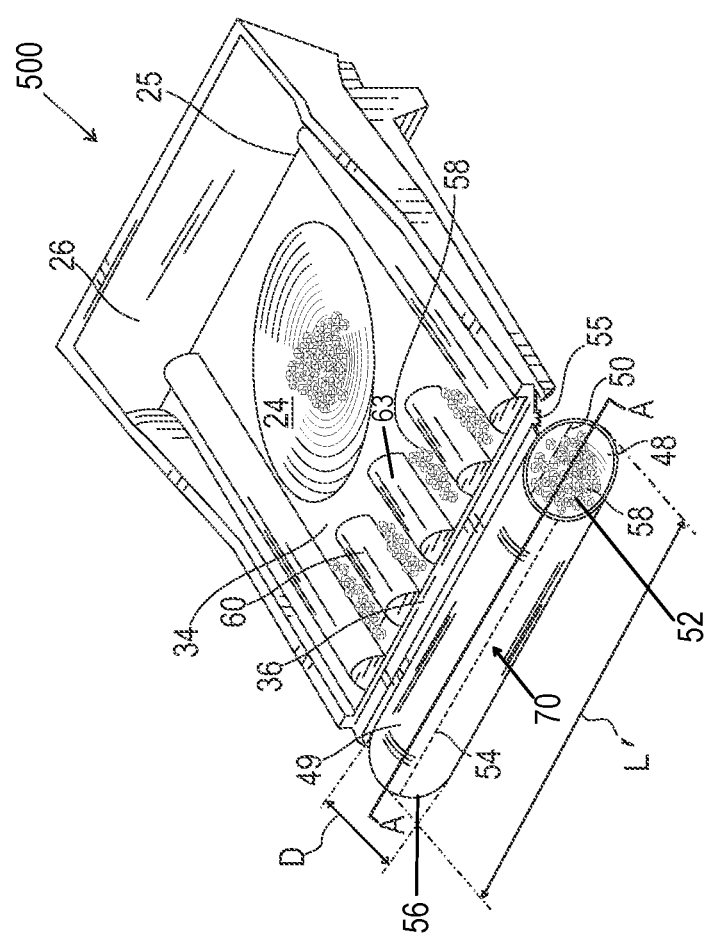
FIG. 6 depicts a perspective view of a bone material dispensing apparatus according to another aspect of the present application where the foldable container is in a folded configuration and the foldable container is loaded with bone material.

Referring to FIG. 6, it illustrates another embodiment of a bone material dispensing apparatus of the present application. The bone material dispensing apparatus comprises a tray 500 that has the foldable container 70 shown in a folded configuration. The tray 500 comprises a proximal end 36, a distal end 25 bordered by a back wall 26. The tray 500 comprises a dispensing surface 34 extending from the distal end 25 to the proximal end 36 of the tray 500 and a mixing surface 24 shown as a bowl configuration to allow mixing of the bone material. In the embodiment shown, the dispensing surface 34 has a plurality of ridges 60 disposed on the dispensing surface 34. Each ridge has a side wall 63, which is spaced a distance apart from each other such that a measured amount of bone material shown as granules 58 is placed between each side wall for measured dispensing of the bone material into the foldable container 70.

In the embodiment shown in FIG. 6, the foldable container 70 has a diameter D and a length L' and is shown in a folded configuration via fold line 54 that can be, for example, a hinge or other rotatable fitting, that allows upper compartment 49 and lower compartment 48 of the foldable container 70 to be folded and partially enclose the bone material 58. Foldable container 70 has an opening at the distal end 52 and an opening at the proximal end 56. These openings, in some embodiments, can be configured to receive a plunger and the plunger would extend along longitudinal axis A. In some embodiments, seam 50 extends longitudinally along axis A and there may be a locking mechanism, which locks the foldable container 70 along the longitudinal axis A. In some embodiments, the foldable container 70 is removably attached to the tray 500 by an attachment member 55. The attachment member 55 extends parallel or substantially parallel to the foldable container 70 and holds the foldable container 70 in place without locking the foldable container 70 completely. This allows easy attachment, filling and removal of the foldable container 70 from the tray 500.

Figure 7:
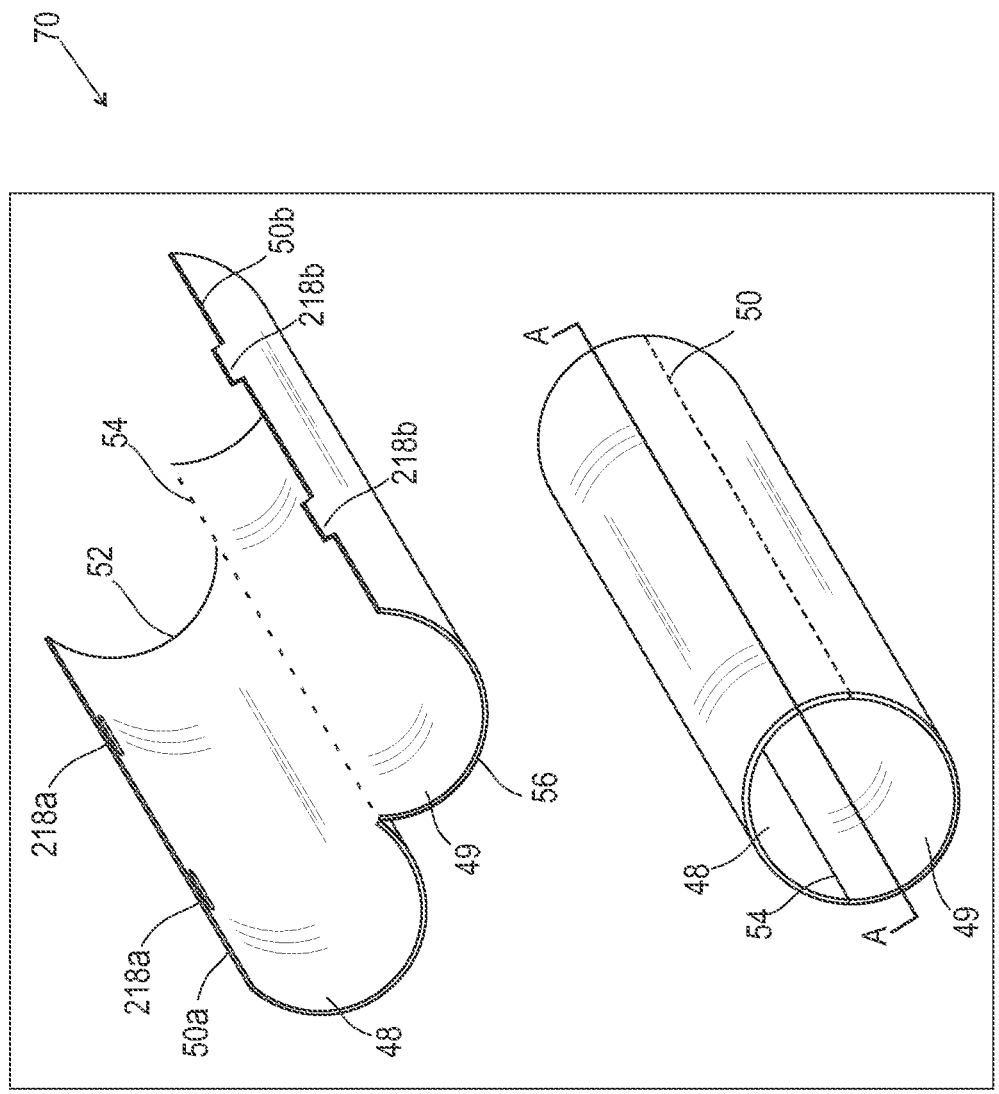
FIG. 7 depicts a perspective view of a foldable container according to an aspect of the present application where the foldable container is in an unfolded configuration and a folded configuration, and the foldable container has slots and tabs for locking the foldable container in the folded configuration.

Referring to FIG. 7, it illustrates a perspective view of the foldable container 70 in the unfolded configuration (shown in the upper panel) and the folded configuration (shown in the lower panel). In the embodiment shown, the foldable container 70 comprises openable seam 50 that separates into two edges, a first edge 50a and a second edge 50b. The first edge 50a is on the lower compartment 48 and the second edge 50b is on the upper compartment 49 of the foldable container 70. The edges have a locking mechanism to lock the upper compartment 49 and lower compartment 48 together. The locking mechanism includes slots 218a, which are adjacent first edge 50a and are spaced apart and correspond to tabs 218b, which are also spaced apart and adjacent second edge 50b. To lock the foldable container 70, first edge 50a and second edge 50b are brought together causing the foldable container 70 to fold via fold line 54 and tabs 218b project outwardly from the exterior to engage and lock into slots 218a to lock the foldable container 70 in a folded configuration. In some embodiments, slots 218a or tabs 218b can correspond to slots and/or tabs on the tray (not shown) to allow the foldable container 70 to removably attach to the tray and provide stability during the dispensing process. In the embodiment shown in FIG. 7, there is an opening at the distal end 52 of the foldable container 70 and an opening at the proximal end 56 of the container 70. These openings, in some embodiments, can be configured to receive a plunger and the plunger would extend along longitudinal axis A.

Figure 8:
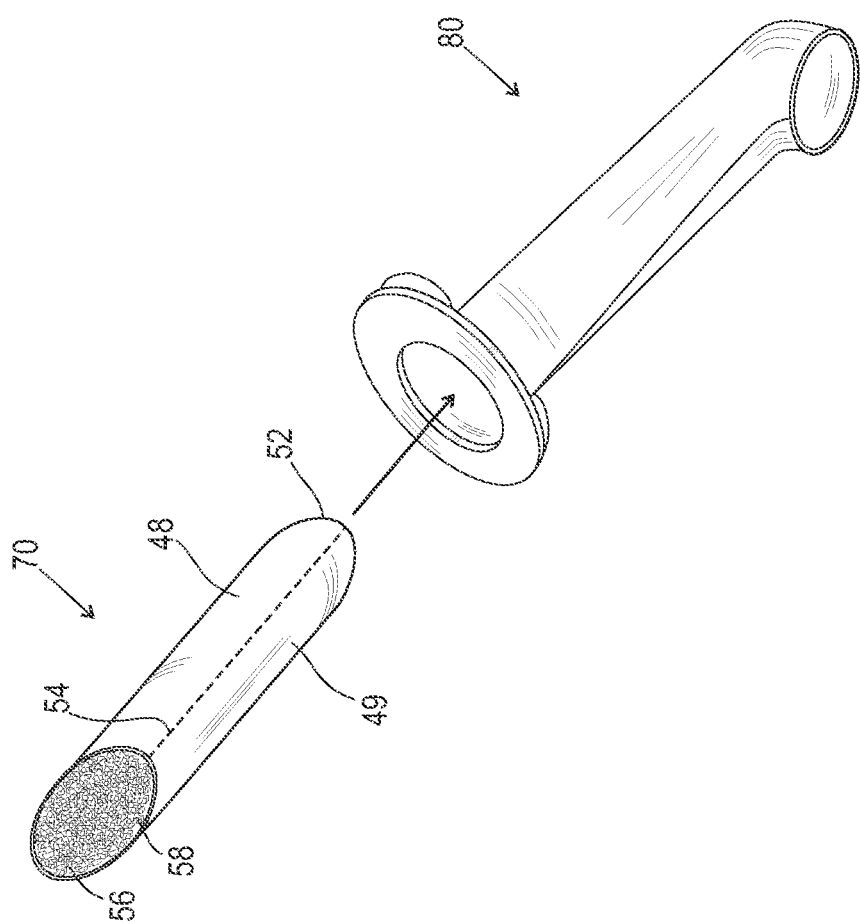
FIG. 8 depicts a perspective view of a foldable container with an insertion device according to an aspect of the present application.

Referring to FIG. 8, it illustrates a perspective view of the foldable container 70 in a folded configuration via fold line 54 that can be, for example, a hinge or other rotatable fitting, that allows the upper compartment 49 and the lower compartment 48 of the foldable container 70 to be folded and partially enclose the bone material shown as granules 58. The foldable container 70 has an opening at the distal end 52 and an opening at the proximal end 56. These openings, in some embodiments, can be configured to receive a plunger.

In some embodiments, the foldable container 70 is configured to be loaded with the bone material 58 and inserted into an insertion device 80, such as for example, a cannula, a needle or a sleeve to allow delivery of the bone material 58 to the target tissue site. The cannula, needle or sleeve is designed to cause minimal physical and psychological trauma to the patient. Cannulas, needles, or sleeves include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The cannula, needle or sleeve may optionally include one or more tapered regions. In various embodiments, the cannula, needle or sleeve may be blunt, beveled, diamond point, ball tip, trocar tip, etc. The cannula, needle or sleeve may also have a tip style vital for accurate treatment of the patient depending on the bone defect. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula, needle or sleeve may also be non-coring and have a sheath covering it to avoid unwanted needle sticks.

In some embodiments, the shape of the tray and the foldable container may be selected for particular applications. Such shape and configuration may include, for example, the basic shape of the tray (e.g., a square shaped box, etc.) and the foldable container (e.g., a tubular shaped container).

Figure 9:
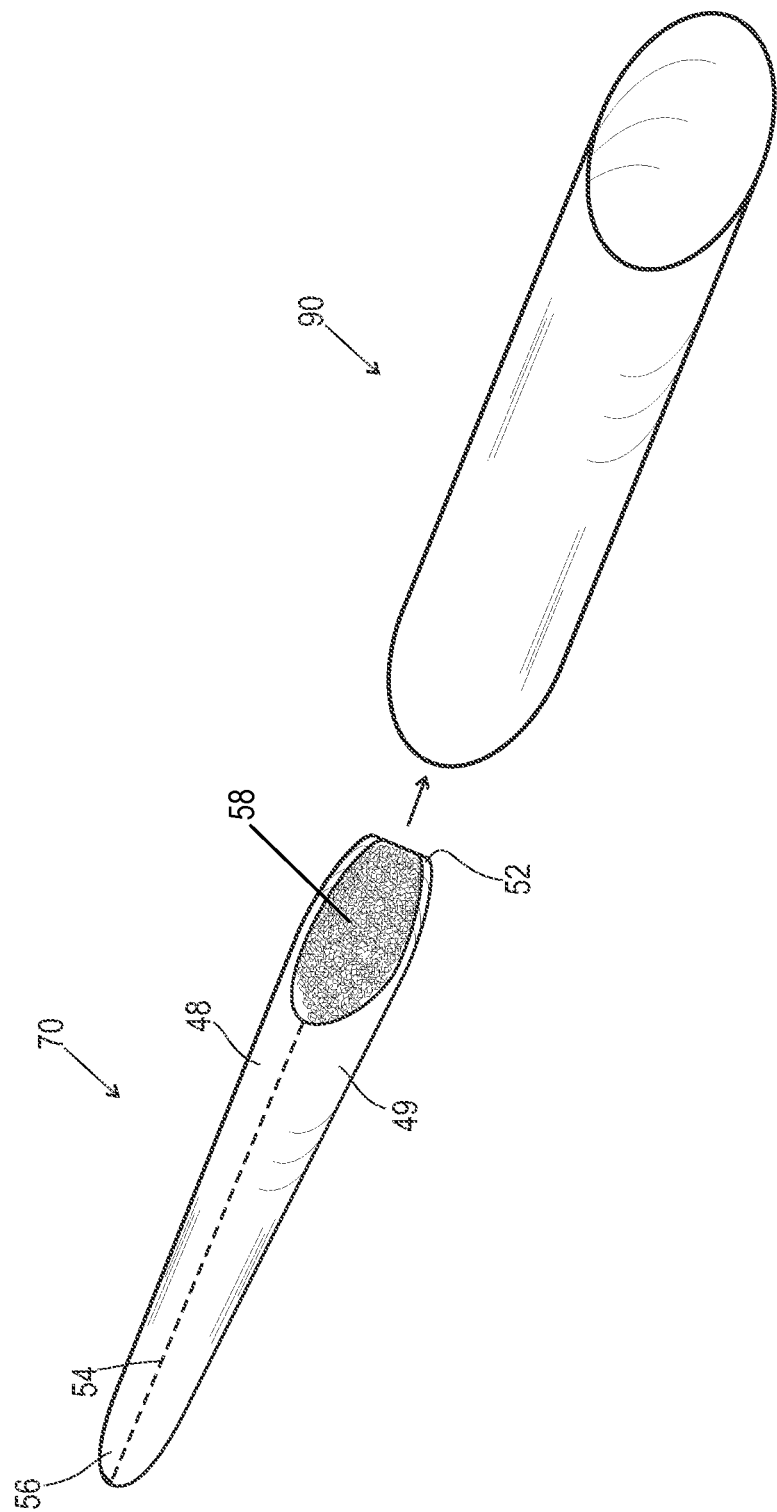
FIG. 9 depicts a perspective view of a foldable container with a sleeve for the container according to an aspect of the present application.

Referring to FIG. 9, it illustrates a perspective view of the foldable container 70 in a folded configuration via fold line 54 that can be, for example, a hinge or other rotatable fitting, that allows the upper compartment 49 and the lower compartment 48 of the foldable container 70 to be folded and partially enclose the bone material shown as granules 58. The foldable container 70 has an opening at the distal end 52 and an opening at the proximal end 56. These openings, in some embodiments, can be configured to receive a plunger. In the embodiment shown, proximal end 56 has a tapered end and when it is slid into a sleeve 90, the foldable container 70 conforms to the sleeve 90 and is locked and closed, whereby inserting a plunger into the proximal end 56 of the foldable container 70, the bone material 58 can be delivered to the bone defect. In some embodiments, the tapered end has a slant opening with an angle from about 0.1 to about 90 degree measuring from the longitudinal axis of the foldable container. Preferably, the slant opening has an angle of about 45 degree. The slant opening ease the insertion of the foldable container into other device with less resistance as the initial contact surface between the foldable container and the other device decreases.

Figure 10:
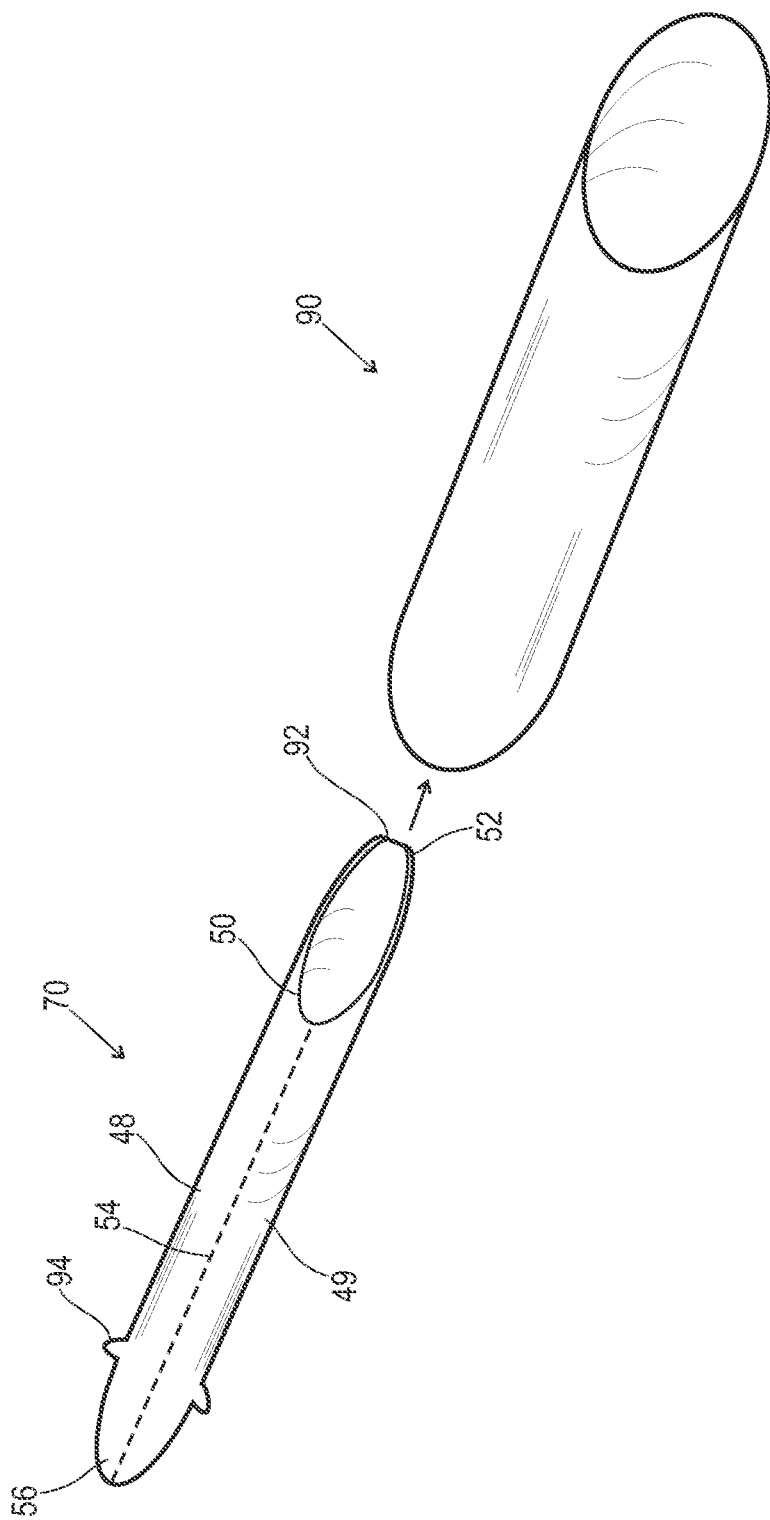
FIG. 10 depicts a perspective view of a foldable container with a sleeve for the container according to another aspect of the present application.

Referring to FIG. 10, it illustrates a perspective view of the foldable container 70 in a folded configuration via fold line 54 that can be, for example, a hinge or other rotatable fitting, that allows the upper compartment 49 and the lower compartment 48 of the foldable container 70 to be folded and partially enclose the bone material. The foldable container 70 has seam 50 and there is an opening at the distal end 52 and an opening at the proximal end 56 of the foldable container 70. These openings, in some embodiments, can be configured to receive a plunger. In the embodiment shown, proximal end 56 and distal end 52 have a tapered configuration. The distal end 52 has and angled tip 92 for ease of insertion into sleeve 90. The foldable container 70 comprises tabs 94 disposed at opposite surfaces of the foldable container 70, which allow the foldable container 70 to be locked and closed in sleeve 90. In some embodiments, the tapered end has a slant opening with an angle from about 0.1 to about 90 degree measuring from the longitudinal axis of the foldable container. Preferably, the slant opening has an angle of about 45 degree. The slant opening ease the insertion of the foldable container into other device with less resistance as the initial contact surface between the foldable container and the other device decreases.

Figure 11:
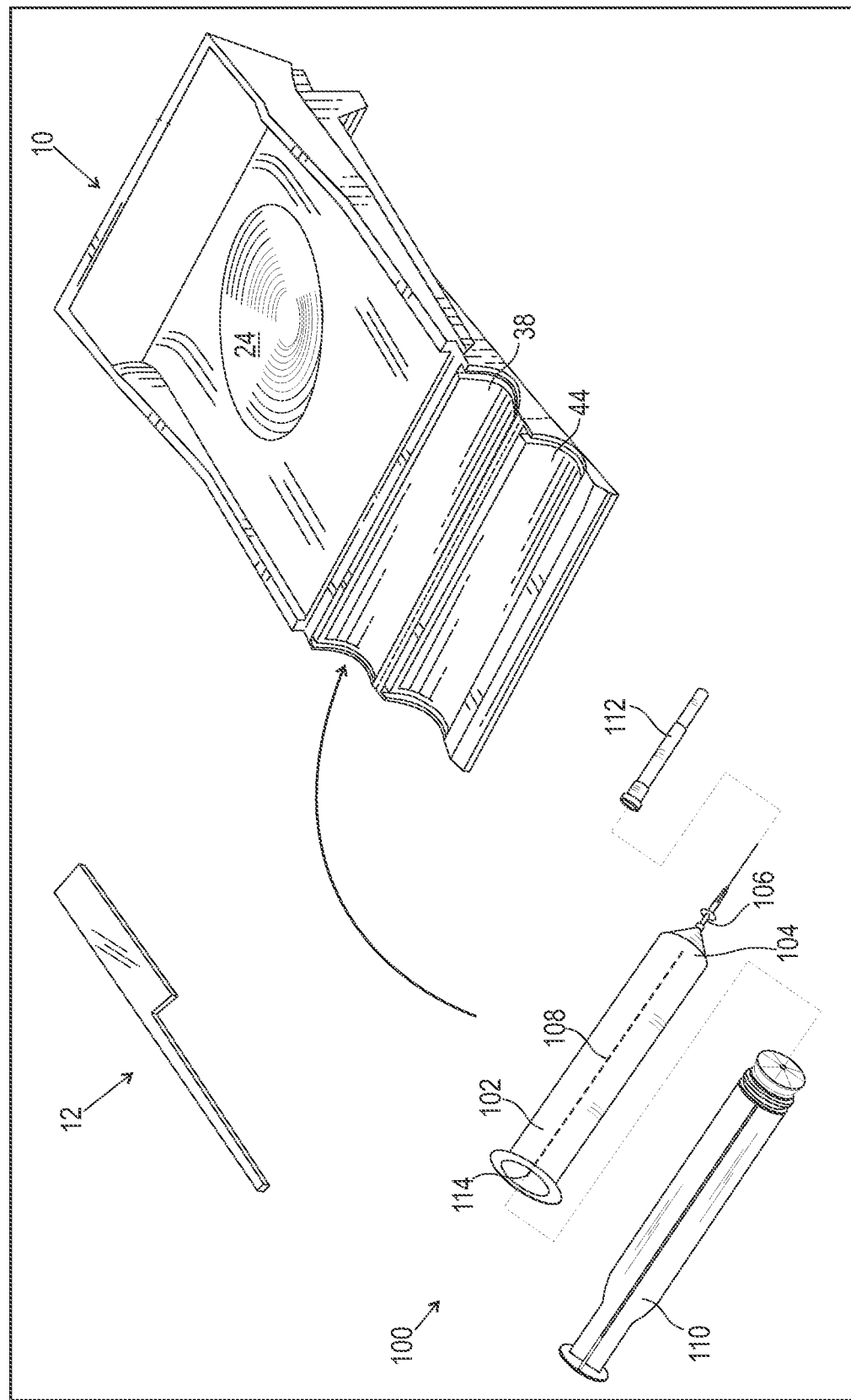
FIG. 11 depicts a perspective view of a bone material dispensing apparatus according to another aspect of the present application, which includes a spatula, foldable container, plunger, needle and needle cover.

FIG. 11 illustrates another aspect of the bone material dispensing apparatus 10 comprising spatula 12 and a tray having the first channel 38 and the second channel 44 that are configured to receive a foldable container 100. The foldable container 100 comprises an upper compartment 102, a lower compartment 104, a fold line 108, an openable seam 114 and a needle 106. The bone material dispensing apparatus 10 further comprises a plunger 110 and a tip cap 112. The plunger 110 allows delivery of the bone material from the bone material dispensing apparatus 10 by sliding the plunger 110 through the loaded foldable container 100 to deliver the bone material out the needle 106 and to the bone defect. In some embodiments, the plunger 110 generally has a smaller diameter compared to the foldable container 100. In some embodiments, the plunger 110 comprises an elongated portion that extends at least the same length as the length of the foldable container 100. The foldable container 100 can be filled with bone material by placing the foldable container in the tray and mixing bone material in mixing surface 24 of the tray and loading the foldable container 100 with bone material when the foldable container 100 is loaded in first channel 38 and second channel 44 of the tray. The foldable container 100 is then assembled with the needle 106 and plunger 110, and the bone material can be delivered to the patient with ease and reduction in clogging of the foldable container 100.

Figure 12:
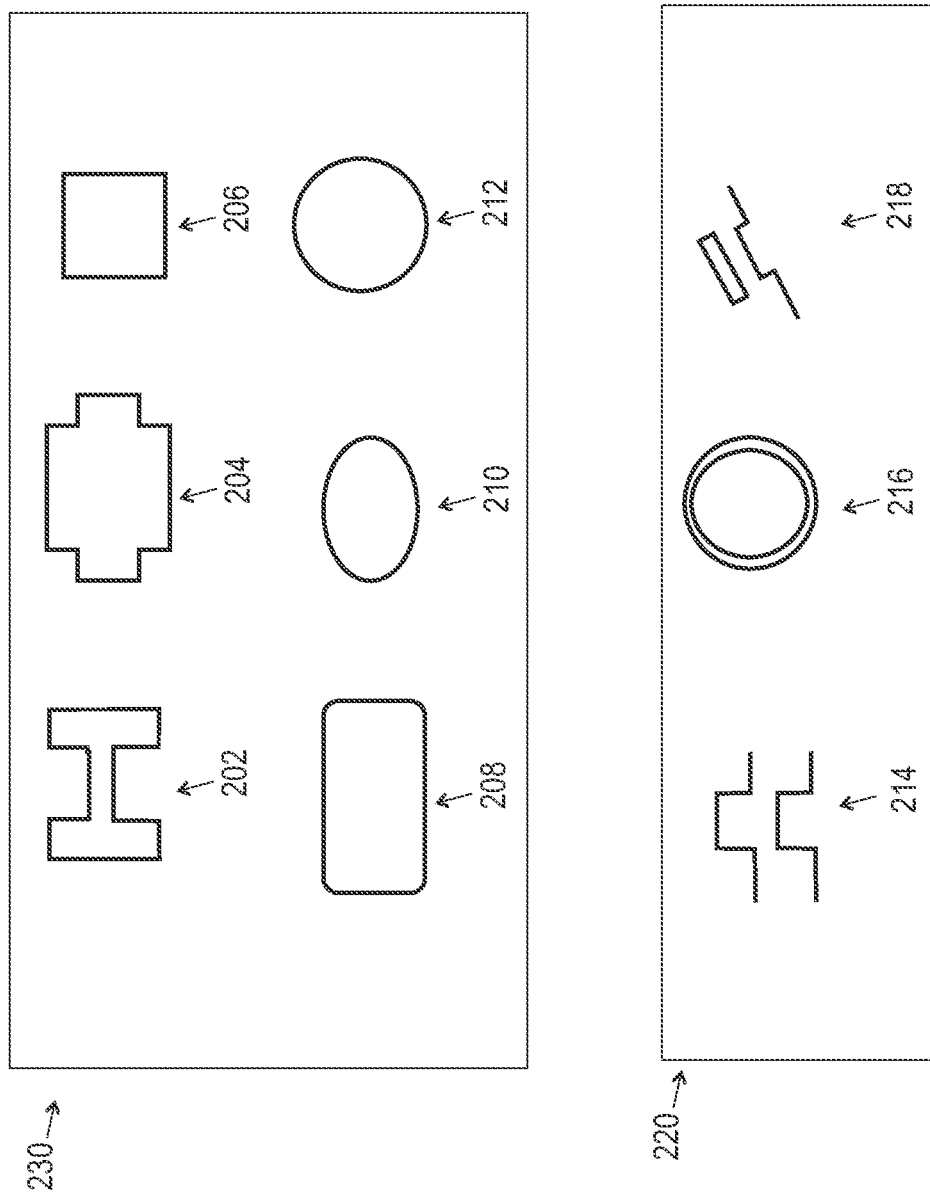
FIG. 12 depicts variously shaped tips that a foldable container can comprise according to an aspect of the present application.
Figure 14:
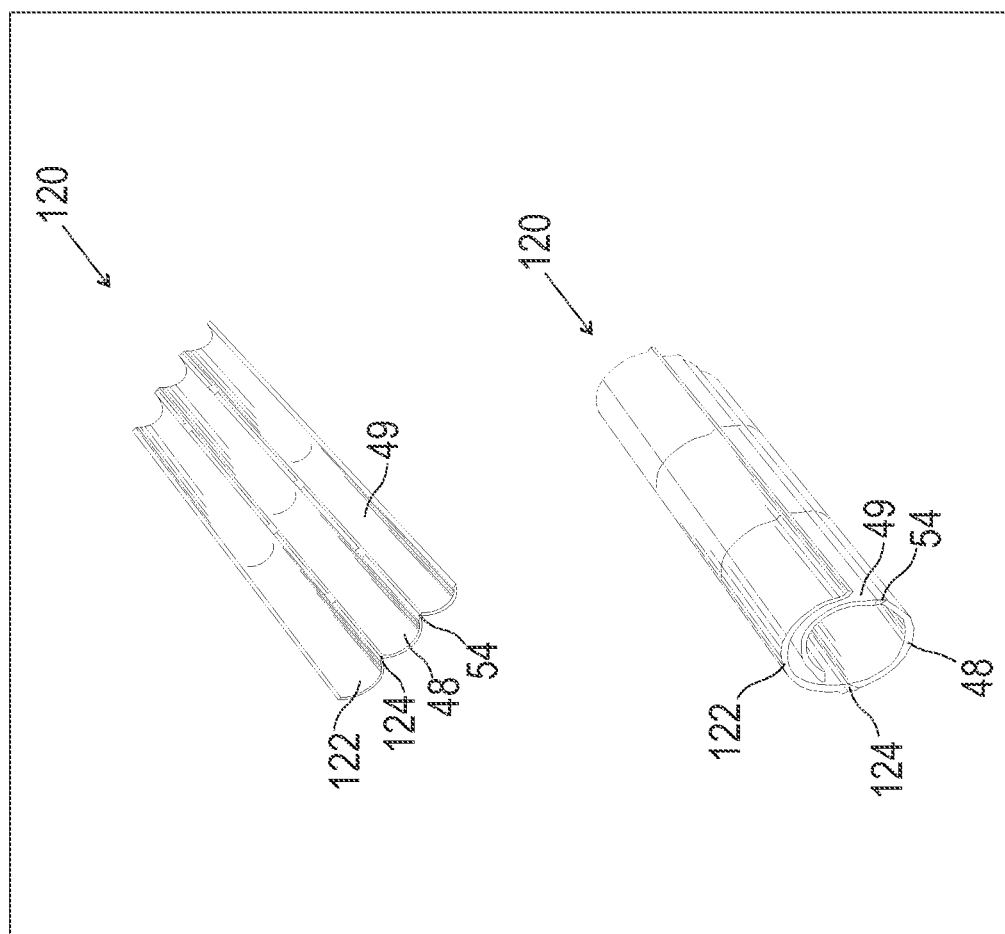
FIG. 14 depicts a perspective view of another embodiment of the foldable container in the open and closed configuration according to another aspect of the present application.

FIG. 12 illustrates a tip 230 of the foldable container. In some embodiments, the tip 230 comprises various shapes including, but not limited to, an H shape 202, clover shape 204, square shape 206, rectangle shape 208, oval shape 210, and circle shape 212. In some embodiments, the tip comprises additional shapes. FIG. 12 further illustrates locking mechanism 220. In some embodiments, the locking mechanism comprises a snap fit fitting 214, a friction fit fitting 216 and a tab-slot fitting 218. In some embodiments, this tip geometry is consistent for the entire length of the folded configuration. In some embodiments, the locking mechanism could include a third and/or a fourth folding element that are connected to the upper and/or lower compartments by additional fold lines. These additional folding elements would enable the user to fold over and secure closed the foldable container. FIG. 14 illustrates a container 120 with a third folding element. In this configuration, the container comprises an upper compartment 49, a lower compartment 48, and a third ½ tube 122. The upper compartment is joined to the lower compartment by a fold line 54. A third ½ tube of slightly larger diameter is joined to the lower compartment by a second fold line 124. In the closed configuration, the upper and lower compartments are loaded with bone material and folded together to create a circular tube. The slightly larger third ½ tube attached to the lower compartment via the second fold line is closed over top of the upper container to lock the folded container closed.

Figure 13:
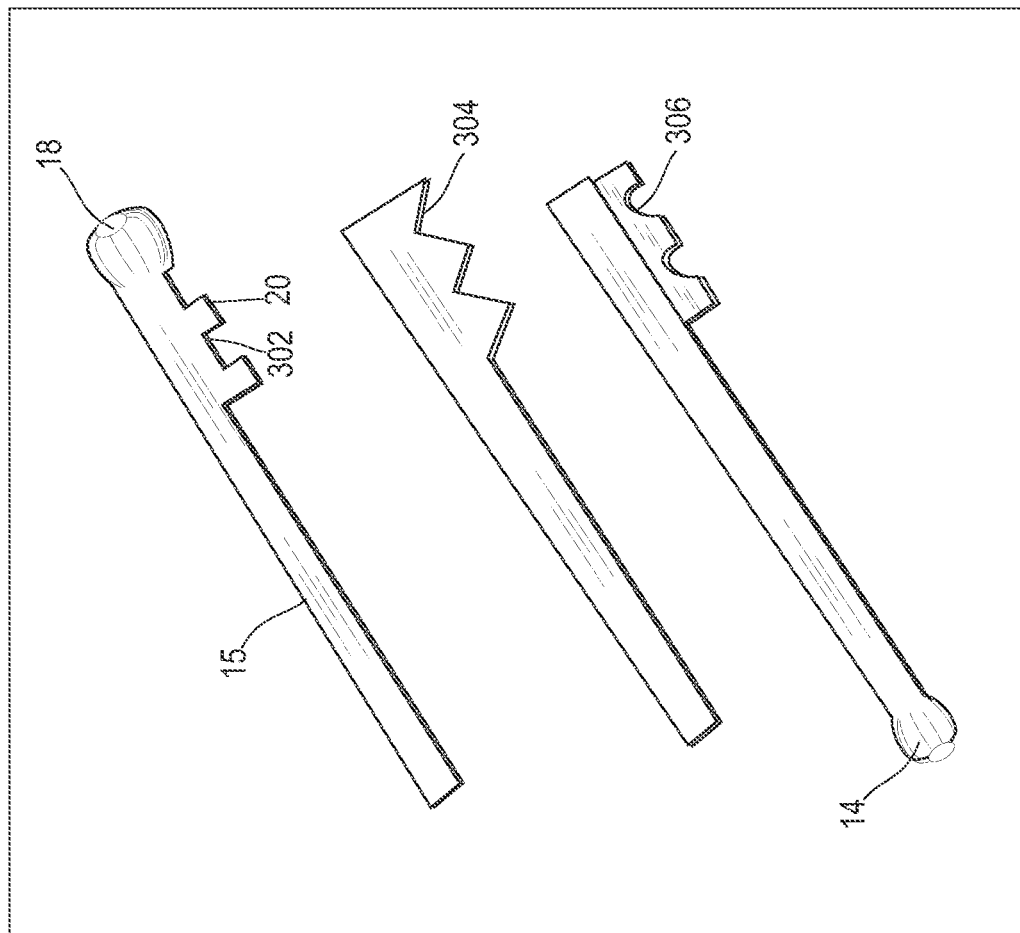
FIG. 13 depicts a perspective view of spatulas according to another aspect of the present application.

FIG. 13 illustrates different spatulas 12, where the body is substantially rectangular or round. The spatula may comprise a tip portion 18 that is configured for grinding and/or mixing bone materials. The spatula may have a distal portion 14 that is configured for grinding and mixing materials. In some embodiments, the blade portion 20 of the spatula comprises various shapes corresponding to the shapes of the ridges and the space between the ridges of the tray. The blade portion may include a rectangular cutout 302 corresponding to a rectangular ridge of the tray, a triangular cutout 304 corresponding to a triangular ridge of the tray, or an arcuate/circular cutout 306 corresponding to an arcuate/circular ridge of the tray. In some embodiments, the number of cutouts may be less than the number of ridges.

In various embodiments, a kit is provided comprising the bone material dispensing apparatus, which includes the tray and the foldable container. The kit may include additional parts along with the bone material dispensing apparatus including the bone material and other components to be used to administer the bone material (e.g., wipes, needles, syringes, other mixing devices, etc.). The kit may include the bone material in a first compartment. The second compartment may include a vial holding the carrier and any other instruments needed for the delivery. A third compartment may include gloves, drapes, wound dressings and other procedural supplies for maintaining sterility of the implanting process, as well as an instruction booklet, which may include a chart that shows how to administer the bone material after mixing it. A fourth compartment may include additional needles and/or sutures. Each tool may be separately packaged in a plastic pouch that is sterilized. A fifth compartment may include an agent for radiographic imaging. A cover of the kit may include illustrations of the implanting procedure and a clear plastic cover may be placed over the compartments to maintain sterility.

In various embodiments, one or more components of the bone material dispensing apparatus is sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply into the bone material dispensing apparatus. Gamma rays are highly effective in killing microorganisms, they leave no residues, nor do they have sufficient energy to impart radioactivity to the apparatus. Gamma rays can be employed when the apparatus is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the bone material dispensing apparatus. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the dispensing apparatus including, but not limited to, gas sterilization such as, for example, with ethylene oxide or steam sterilization.

Methods of Use

A method of filling bone material into a foldable container is provided. The method comprises: placing a bone material in or on a dispensing surface of a tray, the tray having a proximal end, a distal end, and the dispensing surface disposed between the proximal end and the distal end of the tray; transferring the bone material from the dispensing surface of the tray to fill a foldable container with the bone material, the foldable container configured to removably engage the proximal end of the tray, the foldable container being movable in a folded configuration and an unfolded configuration about a fold line in the foldable container, the foldable container having an upper compartment and a lower compartment, the lower compartment of the foldable container configured to receive the bone material from the dispensing surface of the tray when the foldable container removably engages the proximal end of the tray in the unfolded configuration; and folding the upper compartment on the lower compartment of the foldable container to enclose the bone material in the foldable container when the foldable container is in the folded configuration thereby filling the foldable container with bone material.

The bone material can be mixed with liquid material and optionally a therapeutic agent using the spatula, the mixing surface and the dispensing surface of the tray until the desired consistency of the bone material is achieved (e.g., putty, paste, etc.). The bone material can be mixed with a suitable diluent and then loaded into the foldable container. The foldable container may have enough space to allow for the bone material and a volume of diluent to be mixed. In some embodiments, the diluent includes dextrose, other sugars including but not limited to sucrose, fructose, glucose, lactated ringer's, polyols including but not limited to mannitol, xylitol, sorbitol, maltitol, lactitol, polysaccharides including but not limited to native or pre-gelatinized starch, maltodextrins, cyclodextrins, mineral compounds including but not limited to dicalcium or tricalcium phosphate, either dihydrate or anhydrous, cellulose derivatives including but not limited to microcrystalline cellulose, lactoses either monohydrates thereof or anhydrous, as well as their mixtures such as dicalcium phosphate dihydrate, mannitol, pre-gelatinized maize starch, microcrystalline cellulose and their mixtures, water and/or NaCl (saline). In some embodiments, the saline is 0.90% saline or 0.45% saline. In some embodiments, other delivery vehicles can be used for example, D5W (dextrose in 5% water), D5NS (dextrose in 5% water and normal saline) and D5W/½NS (D5W and ½ normal saline), blood, mesenchymal stem cells, or the like.

In some embodiments, the method further comprises removing the filled foldable container from the tray, placing a plunger in the filled foldable container at a proximal opening of the foldable container; placing a needle at a distal opening of the foldable container; inserting the needle at a bone defect; and delivering the bone material from the foldable container to the bone defect. In some embodiments, the method further comprises removing the filled foldable container from the tray; placing the filled foldable container in a delivery cannula; placing a plunger in the filled foldable container at a proximal opening of the foldable container; inserting the delivery cannula at a bone defect; and delivering the bone material in the foldable container to the bone defect.

In some embodiments, the foldable container in an open and unfolded configuration can be rotated horizontally such that the upper compartment and the lower compartment may switch their corresponding positions with the first channel and the second channel. After the upper compartment on the first channel is filled with the bone material, it can be rotated such that the lower compartment will be disposed on the first channel to receive bone materials. In some embodiments, the foldable container in an open and unfolded configuration can be rotated 90 degrees such that the longitudinal axis of the foldable container is perpendicular to the axis formed between proximal end 36 and distal end 25 of the tray. In some embodiments, the longitudinal axis of the foldable container is parallel to a longitudinal axis of the ridge of the tray.

The bone material dispensing apparatus can be used to treat a variety of conditions including osteoporosis, bone fracture repair or healing, dental procedures for which increased bone formation in the jaw is of clinical benefit, repair of craniofacial bone defects induced by trauma or congenital defects such as cleft palate/lip, and a number of other musculoskeletal disorders where native bone growth is inadequate, which will be evident to those of ordinary skill in the art. The bone material can be administered to treat open fractures and fractures at high risk of non-union, and in subjects with spinal disorders, including subjects in need of spine fusion (e.g., anterior lumbar interbody fusion, posterior lumbar spinal fusion, and cervical spine fusion) or subjects having degenerative disc disease or arthritis affecting the lumbar and cervical spine.

Although the invention has been described with reference to embodiments, persons skilled in the art will recognize that changes may be made in form and detail without departing from the spirit and scope of the disclosure.

What is claimed is:

1. A bone material dispensing apparatus, comprising:
a tray having a proximal end, a distal end, a bone material dispensing surface disposed between the proximal end and the distal end of the tray and a container holding surface disposed at the proximal end of the tray adjacent to the bone material dispensing surface;
a foldable container configured to removably engage the proximal end of the tray, the foldable container being movable in a folded configuration and an unfolded configuration about a fold line in the foldable container, the foldable container having an upper compartment and a lower compartment, the lower compartment of the foldable container configured to receive a bone material from the dispensing surface of the tray when the foldable container removably engages the proximal end of the tray in the unfolded configuration and when the foldable container is in the folded configuration, the upper compartment is configured to enclose the bone material in the lower compartment, wherein the proximal end and the distal end of the tray define a longitudinal axis, and the longitudinal axis of the tray is perpendicular to a longitudinal axis of the foldable container formed by a proximal end and a distal end of the foldable container when the foldable container engages the proximal end of the tray; and wherein the container holding surface comprises a first channel and a second channel configured to hold the upper compartment and the lower compartment of the foldable container.

2. The bone material dispensing apparatus of claim 1, wherein the first channel of the proximal end of the tray is dimensioned to correspond to the upper compartment of the foldable container and the second channel of the proximal end of the tray is dimensioned to correspond to the lower compartment of the foldable container such that at least in the unfolded configuration the foldable container is held by the tray.

3. The bone material dispensing apparatus of claim 1, wherein the foldable container has a tubular shaped configuration and a proximal opening configured to receive a plunger and a distal opening configured to receive a cannula or fit within a cannula.

4. The bone material dispensing apparatus of claim 1, wherein the dispensing surface comprises a mixing surface comprising a bowl configured to mix the bone material.

5. The bone material dispensing apparatus of claim 1, wherein the dispensing surface comprises a decline extending from the distal end of the tray to the proximal end of the tray.

6. The bone material dispensing apparatus of claim 1, wherein the dispensing surface comprises a plurality of ridges extending from the distal end to a region adjacent the proximal end, each of the plurality of ridges having a side wall and each of the plurality of ridges spaced a distance apart from each other such that a measured amount of bone material can be placed between each side wall of at least two of the plurality of ridges for measured dispensing of the bone material into the foldable container.

7. The bone material dispensing apparatus of claim 6, the apparatus further comprising a spatula having a blade, the blade having a plurality of projections spaced a distance apart from each other, each projection configured to fit between each side wall of the plurality of ridges so as to allow measured dispensing of the bone material.

8. The bone material dispensing apparatus of claim 1, wherein the fold line comprises a hinge that rotably connects the upper compartment and the lower compartment of the foldable container in the unfolded configuration.

9. The bone material dispensing apparatus of claim 1, wherein the foldable container has a locking mechanism comprising a snap fit fitting, or a projection outwardly extending from an exterior of the foldable container.

10. The bone material dispensing apparatus of claim 1, wherein the foldable container comprises a shape memory polymer.

11. The bone material dispensing apparatus of claim 1, wherein (i) the foldable container has a tubular shape and is configured to receive a plunger at a proximal opening of the foldable container and a needle at a distal opening of the foldable container; or (ii) the foldable container is configured to be inserted into a cannula.

12. The bone material dispensing apparatus of claim 1, wherein the proximal end of the foldable container is configured to receive a plunger, and the foldable container has an exterior having tapering extending from a region of the foldable container to the distal end of the foldable container.

13. The bone material dispensing apparatus of claim 1, wherein the foldable container has a round, oval, rectangular, square, clover or an irregular shaped tip.

* * * * *